US007189401B1

(12) United States Patent
Tracy et al.

(10) Patent No.: US 7,189,401 B1
(45) Date of Patent: Mar. 13, 2007

(54) LIVE ATTENUATED VIRUSES FOR USE AS VECTORS OR VACCINES

(75) Inventors: Steven M. Tracy, Omaha, NE (US); Nora M. Chapman, Omaha, NE (US)

(73) Assignee: University of Nebraska Board of Regents, Lincoln, NE (US)

( * ) Notice: Subject to any disclaimer, the term of this patent is extended or adjusted under 35 U.S.C. 154(b) by 0 days.

(21) Appl. No.: 09/647,911

(22) PCT Filed: Apr. 9, 1999

(86) PCT No.: PCT/US99/07854

§ 371 (c)(1),
(2), (4) Date: Oct. 6, 2000

(87) PCT Pub. No.: WO99/53034

PCT Pub. Date: Oct. 21, 1999

Related U.S. Application Data

(60) Provisional application No. 60/081,138, filed on Apr. 9, 1998.

(51) Int. Cl.
*A61K 39/125* (2006.01)
*C12N 7/01* (2006.01)
*C12N 7/04* (2006.01)
*C12N 15/86* (2006.01)
*C12N 15/41* (2006.01)

(52) U.S. Cl. .............................. 424/199.1; 424/216.1; 424/217.1; 424/93.2; 435/235.1; 435/236; 435/320.1; 536/23.72

(58) Field of Classification Search ............. 424/217.1, 424/199.1, 216.1, 93.2; 435/236, 235.1, 435/320.1; 536/23.72
See application file for complete search history.

(56) References Cited

U.S. PATENT DOCUMENTS 5,869,036 A    2/1999   Belshe et al. ............... 424/93.2

OTHER PUBLICATIONS

Walker et al., Journal of Virology, Dec. 1995, p. 8173-8177.*
Baker et al., Journal of General Virology (1995), 76, 2081-2084.*
Jablonski et al (Journal of Virology 65: 4564-4572, 1991).*
Bell et al, Journal of Virology 73:9413-9421, 1999.*
Parsley et al, Journal of Biological Chemistry 274:12867-12876, 1999.*
Cornell et al, Journal of Virology 78:4397-4407, 2004.*
Cornell et al, Journal of Virology 78:13007-13018, 2004.*
Cornell et al, Virology 298:200-213, 2002.*
Gohara et al, Journal of Biological Chemistry 275:25523-25532, 2000.*
Bowles, N.E. et al., Detection of Coxsackie-B-Virus-Specific RNA Sequences In Myocardial Biopsy Samples From Patients With Myocarditis And Dilated Cardiomyopathy. The Lancet 1120-1122 (1986).
Chapman, N.M. et al., Genetics of Coxsackievirus Virulence. Current Topics in Microbiology and Immunology 223:227-258 (1997).
Domingo, E. and Holland, J.J., RNA Virus Mutations and Fitness for Survival. Annu. Rev. Microbiol. 51:151-178 (1997).
Evans, D.M.A. et al., Increased Neurovirulence Associated with a Single Nucleotide Change in a Noncoding Region of the Sabin Type 3 Poliovaccine Genome. Nature 314:548-550 (1985).
Hansen, J.L. et al., Structure of the RNA-Dependent RNA Polymerase of Poliovirus. Structure 5:1109-1122 (1997).
Jablonski, S.A. et al., Enzymatic Activity of Poliovirus RNA Polymerase Mutants with Single Amino Acid Changes in the Conserved YGDD Amino Acid Motif. Journal of Virology 65:4565-4572 (1991).
Jacobo-Molina, A., et al., Crystal Structure of Human Immunodeficiency Virus Type 1 Reverse Transcriptase Complexed with Double-Stranded DNA at 3.0 Å Resolution Shows Bent DNA, Proc. Natl. Acad. Sci. USA 90:6320-6324 (1993).
Lee, C. et al., Genomic Regions of Coxsackievirus B3 Associated with Cardiovirulence. J. Med. Virol. 52:341-347 (1997).
Macadam, A.J. et al., An Assembly Defect as a Result of an Attenuating Mutation in the Capsid Proteins of the Poliovirus Tyupe 3 Vaccine Strain. Journal of Virology 65:5225-5231 (1991).
Macadam, A.J. et al., Reversion of the Attenuated and Temperature-Sensitive Phenotypes of the Sabin Type 3 Strain of Poliovirus in Vaccinees. Virology 172:408-414 (1989).
Minor, P.D. et al., Genetic Basis of Attenuation of the Sabin Oral Poliovirus Vaccines, Biologicals 21:357-363 (1993).

(Continued)

*Primary Examiner*—Mary E. Mosher
(74) *Attorney, Agent, or Firm*—Woodcock Washburn LLP

(57) ABSTRACT

The present invention provides modified viral genomes for use as vaccines or vectors, which are improved in their ability to retain attenuating mutations. The genomes are from viruses that replicate by way of an RNA-dependent RNA or DNA polymerase. The genomes are modified in the pol gene to encode polymerases that catalyze slower replication, have increased transcriptional fidelity, or are otherwise altered such that the reversion rate of the modified virus to a non-attenuated form is decreased as compared to an equivalent, unmodified virus. In particular, modified coxsackievirus genomes are disclosed.

8 Claims, No Drawings

OTHER PUBLICATIONS

O'Reilly, E.K. and Kao, C.C., Analysis of RNA-Dependent RNA Polymerase Structure and Function as Guided by Known Polymerase Structures and Computer Predictions of Secondary Structure. Virology 252:287-303 (1998).

Oude Essink, B.B., et al., Increased Polymerase Fidelity of the 3TC-Resistant Variants of HIV-1 Reverse Transcriptase. Nucleic Acids Research 25:3212-3217 (1997).

Ramsingh, A.I. and Collins, D.N., A Point Mutation in the VP4 Coding Sequence of Coxsackievirus B4 Influences Virulence. Journal of Virology 69:7278-7281 (1995).

Romero, J.R., et al., Genetic Divergence Among the Group B Coxsachieviruses. Current Topics in Microbiology and Immunology 2232:97-152 (1997).

Rubinek, T. et al., The Fidelity of 3' Misinsertion and Mispair Extension during DNA Synthesis Exhibited by Two Drug-Resistant Mutants of the Reverse Transcriptase of Human Immunodeficiency Virus Type 1 with Leu74→Val and Glu89→Gly. Eur. J. Biochem. 247:238-247 (1997).

Sousa, R. et al., Crystal Structure of Bacteriophage T7 RNA Polymerase at 3.3 Å Resolution. Nature 364:593-599 (1993).

Tracy, S. et al., Genetics of Coxsackievirus B Cardiovirulence and Inflammatory Heart Muscle Disease. Trends in Microbiology 4:175-179 (1996).

Wainberg, M.A., Increased Fidelity of Drug-Seelected M184V Mutated HIV-1 Reverse Transcriptase as the Basis for the Effectiveness of 3TC in HIV Clinical Trials. Leukemia Apr. 11 Supp. 3:85-88 (1997).

Zhang, H. et al., Coxsackievirus b3-Induced Myocarditis: Characterization of Stable Attenuated Variants that Protect Against Infection with the Cardiovirulent Wild-Type Strain. American Journal of Pathology 150:2197-2207 (1997).

Zhang, H.Y. et al., Attenuation of a Recativated Cardiovirulent Coxsackievirus B3: The 5'-Nontranslated Region Does Not Contain Major Attenuation Determinants. Journal of Medical Virology 41:129-137 (1993).

* cited by examiner

LIVE ATTENUATED VIRUSES FOR USE AS VECTORS OR VACCINES

This application is a United States National Phase Application based on International Application PCT/US99/07854, filed Apr. 9, 1999, and claims benefit of U.S. Provisional Application No. 60/081,138, filed Apr. 9, 1998, the entirety of which is incorporated by reference herein.

Pursuant to 35 U.S.C. §202(c), it is acknowledged that the U.S. Government has certain rights in the invention described herein, which was made in part with funds from the National Institutes of Health, Grant No. R21-AI42153.

FIELD OF THE INVENTION

The present invention relates generally to the fields of molecular biology and virology. More specifically, the invention provides modified viruses for use as vaccines or vectors, which are improved in their ability to retain engineered attenuations.

BACKGROUND OF THE INVENTION

Several publications and patents are referenced in this application to describe the state of the art to which the invention pertains. Each of these publications or patents is incorporated by reference herein.

RNA viruses and retroviruses use viral encoded polymerases which have a low fidelity, thereby increasing the number of mutations that occur during replication of the viral genome. This low fidelity results in a virus population that contains a large number of variants. The large variation enables these viruses to rapidly evolve to adapt to a changing environment, such as a reactive immune system, or to lose attenuating mutations introduced to limit replication of the virus in the host.

The RNA-dependent RNA polymerase (RDRP), has an error rate of about $10^{-4}$ (i.e., one error is introduced per every 10,000 nucleotides). Thus, each time the average RNA virus genome (ranging in size from 7,400 to ~20,000 bases) is replicated in either the positive or negative strands, at least one new random error is introduced. Reverse transcriptase (RT) has a similar error rate.

A good example of the negative impact of such a mutation rate can be observed in the Sabin poliovirus vaccine, which is a live, attenuated virus carrying a single primary attenuating mutation in the 5' non-translated region. Within 3–5 days post-vaccination in children, the poliovirus shed in the stool has reverted to a virulent genome and the major attenuating mutation site has changed back to wild-type.

The main factor contributing to high mutation rates in these viruses is the absence or low efficiency of proofreading or repair activities associated with RDRPs. Structurally, the RDRPs are similar to one another (for instance, HIV reverse transcriptase and poliovirus RNA polymerase are quite similar). The poliovirus RNA polymerase is shaped like a hand that is making an effort to hold a cup or glass, fingers somewhat together and curled, thumbs apart, with a palm in between (see, e.g., Hansen, J. L., A. M. Long and S. C. Schulz (1997); Structure 5: 1109–1122). The palm region contains the active site for both the poliovirus and HIV polymerases, and the region contains similar motifs in both enzymes. In HIV strains from patients who no longer respond to nucleotide therapy, mutants have been isolated that (a) have mutations in the palm region, (b) show many-fold (e.g., 3–49 fold) better fidelity, and (c) replicate the genome at a reduced rate.

Clearly, the aforementioned high reversion rate in RNA viruses and other viruses utilizing RDRPs or RTs, which is caused by their low-fidelity polymerases, is detrimental to their utility as vaccines or as vectors for delivery of other genes of interest. Thus, the field of viral vaccines and vectors would be vastly improved through the development of improved vectors encoding RDRPs or RTs with greater replicative fidelity, such that attenuations introduced into the viral genomes are retained for longer periods of time, without reversion to wild-type virus.

SUMMARY OF THE INVENTION

The present invention provides novel modified viral genomes that encode RDRPs and RTs whose activity is altered, e.g., by having improved fidelity as compared with their unmodified counterparts. When combined with additional attenuation mutations, these genomes and their encoded viruses are superior to those currently available for use as vaccines or as vectors for delivery of other genes of therapeutic or diagnostic value.

In one aspect of the invention, there is provided a virus genome that encodes an RNA-dependent polymerase, the genome being modified to produce an attenuated virus, the genome further comprising at least one pol gene modification, which results in a decreased reversion rate from attenuated virus to non-attenuated virus as compared with an equivalent virus genome without the pol gene modification. The RNA-dependent polymerase can be an RNA polymerase or a reverse transcriptase. Preferably it is an enterovirus genome, more preferably a coxsackievirus genome. The decreased reversion rate can be the result of a variety of alterations in the polymerase, such as a decrease in rate of polymerase activity, which itself may be caused by the enzyme having increased fidelity as compared with a polymerase from a virus genome that does not comprise the pol gene modification.

According to another aspect of the invention, a viral vector for delivering a heterologous nucleic acid to a target cell, tissue or organ is provided. The vector comprises the aforementioned modified virus genome, and further comprises at least one cloning site for insertion of an expressible heterologous nucleic acid, such as an antigen or a biologically active molecule.

According to another aspect of the invention, the modified virus may be used as a live, attenuated vaccine for prevention of infection by that virus.

In a preferred embodiment of the present invention, the polymerase-modified viral genome described above is a coxsackievirus genome, preferably a coxsackievirus 3B (CVB3) genome, modified to produce an attenuated virus. In the CVB3 genome, the pol gene modification preferably comprises a mutation at a position on the genome encoding glycine 328. The attenuation mutation of the coxsackievirus genome preferably is in a transcription regulatory region, such as the 5' non-translated region of the genome. The CVB3 genome of claim 16, wherein the modification to produce an attenuated virus comprises altering a transcription regulatory region of the genome. Most preferably, the genome is modified by changing U to C or G, or C to G, at nucleotide position 234 of the genome to achieve the attenuation. In alternative embodiments the genome contains other attenuating mutations, or a combination of attenuating mutations, along with the pol gene modification.

Other features and advantages of the present invention will be better understood by reference to the drawings, detailed descriptions and examples that follow.

DETAILED DESCRIPTION OF THE INVENTION

I. Definitions

Certain aspects of the present invention employ conventional molecular biology, microbiology, and recombinant DNA techniques that are well known in the art. See, e.g., Sambrook et al., "Molecular Cloning: A Laboratory Manual" (1989); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription and Translation" [B. D. Hames & S. J. Higgins eds (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984); or "Current Protocols in Molecular Biology", eds. Frederick M. Ausubel et al., John Wiley & Sons, 1999.

Therefore, if appearing herein, the following terms have the definitions set out below.

A "coding sequence" or "coding region" refers to a nucleic acid molecule having sequence information necessary to produce a gene product, when the sequence is expressed.

The term "operably linked" or "operably inserted" means that the regulatory sequences necessary for expression of the coding sequence are placed in a nucleic acid molecule in the appropriate positions relative to the coding sequence so as to enable expression of the coding sequence. This same definition is sometimes applied to the arrangement other transcription control elements (e.g. enhancers) in an expression vector.

Transcriptional and translational control sequences are DNA regulatory sequences, such as promoters, enhancers, polyadenylation signals, terminators, and the like, that provide for the expression of a coding sequence in a host cell.

The terms "promoter", "promoter region" or "promoter sequence" refer generally to transcriptional regulatory regions of a gene, which may be found at the 5' or 3' side of the coding region, or within the coding region, or within introns. Typically, a promoter is a DNA regulatory region capable of binding RNA polymerase in a cell and initiating transcription of a downstream (3' direction) coding sequence. The typical 5' promoter sequence is bounded at its 3' terminus by the transcription initiation site and extends upstream (5' direction) to include the minimum number of bases or elements necessary to initiate transcription at levels detectable above background. Within the promoter sequence is a transcription initiation site (conveniently defined by mapping with nuclease S1), as well as protein binding domains (consensus sequences) responsible for the binding of RNA polymerase.

A "vector" is a replicon, such as plasmid, phage, cosmid, or virus to which another nucleic acid segment may be operably inserted so as to bring about the replication or expression of the segment.

An "origin of replication" refers to those DNA sequences that participate in the in the initiation of DNA synthesis.

A cell has been "transformed" or "transfected" by exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

A "heterologous" region of a nucleic acid construct is an identifiable segment of the nucleic acid molecule within a larger molecule that is not found in association with the larger molecule in nature. Thus, when the heterologous region encodes a mammalian gene, the gene will usually be flanked by DNA that does not flank the mammalian genomic DNA in the genome of the source organism. In another example, coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

The terms set forth below, relating to the biological molecules and methods of the present invention, are used throughout the specifications and claims.

The term "Coxsackie B3 virus;" or "CVB3" refers to a specific serotype of the human coxsackie B enterovirus of the family Picornaviridae, genus *Enterovirus*. The CVB3 genome is characterized by a single molecule of positive sense RNA which encodes a 2,185 amino acid polyprotein.

The term "attenuated" refers to a virus that is modified to be less virulent (disease-causing) than wildtype virus.

The term "basic CVB3/0 genome" refers to the modified Coxsackievirus B3 as reported by Chapman, N. M., et al, *Arch. Virol.* 122:399–409 (1994).

The term "viral protease" or "viral encoded protease" refers to viral encoded enzymes that degrade proteins by hydrolyzing peptide bonds between amino residues. Some such proteases recognize and cleave at only specific sequences.

The term "open reading frame" refers to a length of RNA or DNA sequence, between a translation start signal (e.g., AUG or ATG) and any one or more of the known termination codons, which encodes one or more polypeptide sequences.

The term "RNA-dependent polymerase" (RDP) refers to a viral polymerase that transcribes either RNA or DNA from an RNA template. The RNA viruses described herein produce an RNA-dependent RNA polymerase (RDRP). The retroviruses described herein produce an RNA-dependent DNA polymerase, often referred to as a "reverse transcriptase (RT)"

The term "viral vector" refers to a virus that is able to transmit foreign or heterologous genetic information to a host. This foreign genetic information may be translated into a protein product, but this is not a necessary requirement for the foreign information.

The term "capsid coding region" refers to that region of a viral genome that contains the DNA or RNA code for protein subunits that are packaged into the protein coat of the virus particle.

II. Compositions and Methods

RNA viruses and retroviruses use viral encoded polymerases RNA-dependent polymerases (RDPs) which have a low fidelity, thereby increasing the number of mutations that occur during replication of the viral genome. The low fidelity of these RDPs negatively impacts the effectiveness of these viruses as vectors or vaccines, because they quickly lose attenuating mutations introduced to limit replication of the virus in the host. The present invention is directed to modifications of the genomes of these viruses to improve the fidelity of their RDPs, thereby reducing the rate of reversion of attenuated strains and slowing the replication rate of attenuated viruses being used as vaccines or vectors.

Any virus having utility as a vaccine or vector, which replicates by means of a RNA-dependent polymerase, is suitable for modification in accordance with the present invention. Examples of suitable viruses include, but are not limited to, enteroviruses such as coxsackieviruses, echoviruses, polioviruses and numbered enteroviruses, other RNA viruses such as flaviviruses and togaviruses, and retroviruses such as human immunodeficiency virus (HIV), human T-cell leukemia virus (HTLV), avian sarcoma leukosis virus (ASLV), feline leukemia virus (FeLV), bovine immunodeficiency virus (BIV) and equine infectious anemia virus (EIAV), among others. Other suitable viruses can be selected from the families of mammalian viruses known to replicate using an RNA-dependent polymerase. These include picornaviruses, calciviruses, coronaviruses, retroviruses, flaviviruses, togaviruses, filoviruses and bunyaviruses.

The RDPs of the above-listed viruses are structurally similar to one another, as demonstrated by reference to the following representative published literature: Jacobo-Molina A, Ding J, Nanni R G, Clark A D Jr, Lu X, Tantillo C, Williams R L, Kamer G, Ferris A L, Clark P, et al., (1993) Crystal structure of human immunodeficiency virus type 1 reverse transcriptase complexed with double-stranded DNA at 3.0 A resolution shows bent DNA. Proc Natl Acad Sci USA 90(13):6320–4; Hansen J L, Long A M, Schultz S C, (1997) Structure of the RNA-dependent RNA polymerase of poliovirus. Structure 5(8):1109–22; Sousa R, Chung Y J, Rose J P, Wang B C, (1993) Crystal structure of bacteriophage T7 RNA polymerase at 3.3 A resolution. Nature Aug 12;364(6438):593–9; and O'Reilly E K, Kao C C, (1998) Analysis of RNA-dependent RNA polymerase structure and function as guided by known polymerase structures and computer predictions of secondary structure. Virology 252 (2):287–303.

Attenuated coxsackieviruses are contemplated as being particularly useful for practice of the present invention. Methods for making modified coxsackievirus genomes with primary attenuating mutations are described in detail in co-pending U.S. Ser. No. 08/812,121 and co-pending PCT Serial No. PCT US98/04291, both to Tracy and Chapman, the disclosures of which are incorporated by reference herein. Those patent documents describe a viral vector which comprises a coxsackievirus genome modified to encode an attenuated coxsackievirus, preferably a coxsackievirus B, most preferably a coxsackievirus B3.

Tracy and Chapman teach that attenuation of the coxsackievirus can be achieved by altering a transcription regulatory region of the genome. Preferably, the transcription regulatory region comprises a 5' untranslated region of the genome. In one instance, the 5' untranslated region is replaced with a 5' untranslated region of a non-enterovirus genome selected from the group consisting of poliovirus and echovirus. In another instance, a coxsackievirus B3 genome is modified by substituting a C or G for a U at nucleotide position 234 of the genome. Another modification includes point mutations at positions nt232 and nt236, or deletion entirely of nt 232–236.

Tracy and Chapman further teach a cloning site in the coxsackievirus vector, which can be positioned between a coding sequence for the capsid protein and a coding sequence for the viral protease. Alternatively, the cloning site is positioned at the start of the genome's open reading frame, and is constructed such that the inserted expressible heterologous DNA comprises a translation start codon and a 3' sequence recognized by a viral protease.

Though coxsackievirus B3 is exemplified herein, any coxsackievirus genome is believed to be suitable for use in the present invention. This is due to the high level of structural similarity among RDPs, as discussed above, as well as substantial organizational similarity among the coxsackieviruses, and indeed among enteroviruses in general (see, e.g., Romero et al., *Current Topics in Microbiology and Immunology* 223: 97–152, 1997; Chapman et al., *Current Topics in Microbiology and Immunology* 223: 227–258, 1997; and Tracy et al., *Trends in Microbiology* 4: 175–179, 1996).

Attenuated strains of viruses other than coxsackieviruses are also contemplated for use in the present invention. Some of these are based on information obtained through characterization of attenuating mutations of poliovirus (Minor P D, Macadam A J, Stone D M, Almond J W, (1993) Genetic basis of attenuation of the Sabin oral poliovirus vaccines. Biologicals Dec; 21(4):357–63). The best defined sites of attenuation in the Sabin strains of poliovirus are those in the Sabin poliovirus 3 strain: the site in the 5' non-translated region causes a reduction in initiation of translation and the sites in the capsid protein encoding region cause a change in stability of the capsid (Macadam A J, Ferguson G, Arnold C, Minor P D, (1991) An assembly defect as a result of an attenuating mutation in the capsid proteins of the poliovirus type 3 vaccine strain. J Virol 65(10):5225–31). In other strains there are sites elsewhere that contribute to attenuation but all the strains contain the 5' non-translated region sites. The majority of the attenuation of all poliovirus strains is due to similar 5' non-translated region sites and capsid sites. As discussed above, attenuation of CVB3 has been made by substituting the 5' non-translated region of poliovirus for the naturally occurring coxsackievirus 5' region. Similar sorts of mutations as found in the polioviruses can be made in the coxsackievirus genome with an expectation of similar results. Alternatively, the 5' non-translated region of attenuated polio-like viruses could be substituted for the coxsackievirus 5' non-translated regions. Such polio-like viruses have a 5' non-translated region sufficiently similar to polioviruses (coxsackieviruses A21 and A24) that similar attenuating mutations can be made with assurance that similar attenuation will occur.

Other candidate viruses particularly suitable for attenuation in a manner similar to that shown for poliovirus and coxsackievirus, then modified in RDP function in accordance with the present invention, include other human enteroviruses such as echoviruses, animal enteroviruses, such as bovine enterovirus, as well as members of the flavivirus and togavirus families. Retroviruses that may be used are animal retroviruses capable of replicating in human cells, or animal retroviruses for use as animal vectors, as well as highly genetically engineered strains of HIV. However, as mentioned above, any virus having an RNA-dependent polymerase is considered suitable for use in the present invention.

Modified viral genomes having a reduce rate of reversion from attenuated mutant to wild-type, via improved transcriptional fidelity, can be selected or identified by two general approaches. In one approach, new viral mutants can be made using methods designed to force preferential mutations in the pol gene. For instance, virus is grown in the presence of ribonucleoside analogs (antiviral drugs) which inhibit the RDPs. Mutations (occurring naturally due to the high error rate and likely to be in the RDP-encoding region in sites similar to the drug resistance sites in HIV) which confer resistance to the ribonucleoside analogs would be selected for in this environment. Viruses with these mutations would out-compete the non-resistant viruses in the presence of the antiviral drug. Viruses are plaque-isolated after several passages in the selective media.

RDPs from mutant viruses are then obtained by RT-PCR, and those genes are used to replace the wild-type RDP coding region in a clone of the viral genome. The clones are used to raise a population of virus in an appropriate cultured cell line (e.g., HeLa cells) and the fidelity is assessed by (1) transcriptional assays that determine the frequency of incorrect rNTP incorporation, and (2) the time required for another mutation (located elsewhere in the genome, such as those we have characterized that slow growth within the viral 5' non-translated region) to revert in the virus with the mutated RDP, as compared to the wild-type RDRP virus containing the same mutation.

In another approach, specific mutations are introduced, or mutations are randomly introduced in a selected region of the RDP coding region known to influence transcriptional fidelity. For instance, mutations may be introduced in the codon at nucleotides 6893–6895 (GGT) which encodes amino acid 328 of the 3D RNA-dependent RNA polymerase, glycine. The preferred mutations are GGT ->AGT (to serine), ->TGT (to cysteine), ->GCT (to alanine). These mutations have been demonstrated to be viable in poliovirus but not lethal, yet with diminished polymerase activity, a phenotype that is consistent with a polymerase with greater fidelity (Jablonski S A, Luo M, Morrow C D, J Virol 65:4565–72, 1991. Accordingly, these mutations can be introduced into coxsackievirus or the other viruses listed above, with the anticipated results being similar to those observed in poliovirus.

In other embodiments, additional mutations suggested by reverse transcriptase higher fidelity mutants are mutations of the aforementioned codon to CTT (leucine) and to ATT (isoleucine) and mutations of the preceding codon (n6890–6892 TAT encoding tyrosine) to TTT (phenylalanine).

As another example, in HIV-1 reverse transcriptase, a met-val substitution at codon 184 is known to improve the fidelity of the transcriptase (Wainberg, M. A. (1997); Leukemia, Apr. 11 Supp. 3: 85–88; Oude Essink, B. B., N. K. T. Back and B. Berkhout (1997); Nucl. Acids Res. 25: 3212–3217). Sites in the finger region of the polymerase also have been shown to affect fidelity; these include leu-val and glu-gly substitutions at codons 74 and 89, respectively (Rubinek, T., M. Bakhanashvili, R. Taube, O. Avidan and A. Hizi (1997); Eur. J. Biochem. 247: 238–247). Similar mutations introduced into enterovirus RNA polymerases are expected to have a similar effect, due to the close structural and sequence homology among the RDPs. For instance, a site in the coxsackievirus B3 genome that corresponds to the leu-val substitution in the RT is position 194 of the CVB3 genome, nucleotides 6491–6493; and a site in CVB3 corresponding to the glu-gly substitution is position 213, nucleotides 6548–6550. In alternative embodiments, these sites are mutated to produce a modified virus with a reduced rate of reversion from attenuated to wild type form.

Mutations are obtained by PCR, discarding nonsense mutations identified by sequence analysis. Specific mutant sequences are then used as described above to replace wild-type sequences in clones of the genomes. Virus is obtained by transfection of the genomes in a cultured cell line, and transcriptional fidelity is assayed as described above.

Consistent with the approaches described above (particularly as demonstrated by the above-mentioned assay for reversion of a second site on the genome) incorporation of sequences encoding higher fidelity RDPs will result in a virus that does not as rapidly correct mutations by the mechanism of stochastic mutation and selection of a more fit (reverted) virus population. If such mutations are primary attenuating mutations, then the resultant attenuated viral genome will be less prone to reversion to wild-type (presumably virulent). A more stable viral strain genome, for use as either a vaccine or a vector, is superior by virtue of reduced risk of reversion and resultant vaccine-related disease caused by the reverted strain. Additionally, any vaccine that is shed in feces, blood or aerosol would more likely be the attenuated strain rather than a reverted, possibly virulent, strain.

Methods for measuring the reversion rate of an attenuated virus in cultured cells and in vivo are described in Example 2. Essentially, these methods measure delays in reversion of an attenuating mutation in viruses containing a selected RDP mutation, as compared with viruses not containing the mutation. An RDP mutant virus exhibiting any observed delay in such reversion, no matter how small, is considered to be within the scope of the present invention. Preferred embodiments of the invention, however, include viruses exhibiting at least a two-fold delay in reversion time, as compared to their RDP-unmodified counterparts. In particularly preferred embodiments, the delay in reversion rate would be greater; e.g., 3–5, 6–8, 9 or 10-fold or more.

The following examples are provided to describe the invention in greater detail. They are intended to illustrate, not to limit, the invention.

EXAMPLE 1

Characterization of a CVB3 Reporter Mutant to Test for Reversion of Mutant Sites This example describes a CVB3 reporter mutant, useful to test modifications of the pol gene for their effect on the rate of reversion of attenuated mutants to wild-type virus.

An infectious, but non-cardiovirulent strain of CVB3 is CVB3/0 (Chapman et al., (1994) Arch. Virol. 135(1–2): 115–130). CVB3/0 differs from the infectious, cardiovirulent strain CVB3/20 by eight amino acid sequence differences; however, the cardiovirulent phenotype of CVB3/20 is determined at a single site in the genomic 5' non-translated region (Tu et al., (1995) J. Virol. 69(8): 4607–4618).

CVB3/20 also contains an attenuating mutation at nt234 (U-G). The reversion rate of this mutation to the wild-type has been characterized in vitro in CVB3/20. It has been found that 234G mutation rapidly reverts to U in passage in HeLa cells. At 37° C., the reversion occurs within 3–4 passages. However, transfection of the plasmid construct at 33.5° C. maintained the mutation intact, judging by sequence analysis of the 234G virus population RNA using RT/PCR and sequencing of the amplimer obtained.

The CVB3/20 mutant with 234G has been demonstrated to be significantly attenuated in terms of replication in both HeLa cells as well as in murine fetal heart fibroblast cultures; Because the virus is attenuated for replication in HeLa relative to the parental CVB3/20, it is expected that the 234G virus is also attenuated for replication in other human cell cultures that may be used.

The biology of mutations in the CVB3 genome in the 5mer surrounding the 234 site (nucleotides 232–236, 5'-CG UUA where 234U [the 5' U] is underlined) have been further elucidated. The inventors have observed that transfection of viruses with mutations in this 5mer at 37° C. results in slow growing, nearly undetectable viruses for the first 2–3 passages in HeLa cells, then a sudden increase in titerable virus. This increase correlates directly with a reversion from the mutation to the wild-type sequence. However, if transfections are performed at 33.5° C. and the stocks are passaged at 33.5° C., the virus population achieves a titerable level within passage 2–3 and also maintains the mutation judging by sequence analysis of the amplimer obtained using total viral RNA as the template. Thus, it would be expected that pol mutations introduced into the viral genome will be stable or more stable when transfected at 33.5° C., and that a delay in reversion of the 234G to U would be observed, compared to the 234G mutant alone (no pol mutation in the same virus) when the virus stocks are shifted to be passaged at 37° C.

Even though the biology of the nt234 mutation has been elucidated in CVB3/20, CVB3/0 is preferred over CVB3/20 as it confers some advantages in the manipulation of the genome but also because it plaques on HeLa cell monolayers, whereas CVB3/20 does not. The genome of CVB3/0 has a C at nt234, which confers attenuation on this clone (Tu et al., 1995, supra). However, from research on CVB3/20, it is known that the G mutation at nt234 confers a greater attenuation than does the C at that position. For this reason, a C-G mutation at nt234 has been introduced into the pCVB3/0 virus genome clone. The CVB3/0 nt234G attenuated mutant is particularly suited for use as a reporter for study of pol mutation because it is highly attenuated in terms of viral replication and the virus can be plaqued.

EXAMPLE 2

Testing CVB3 Vectors Having Modifications Expected to Produce High Fidelity Polymerases This example describes how a CVB3 attenuated, pol modified virus, such as the one described in Example 1, is tested for rate of reversion to wild-type virus in cultured cells and in vivo. In cultured cells, the following assays are used: (a) rapidity of the appearance of cytopathic effects, using light microscopy examination of infected cultures; (b) titer of virus in infected cultures; and (c) RT-PCR amplification of the region surrounding nucleotide 234 and sequence analysis across the mutation. Concurrently, site in the pol gene which the mutation was induced is also sequenced.

Virus is passaged on 100,000 HeLa cells in a monolayer at an MOI (multiplicity of infection) of infectious virus particles (defined in TCID50) of 1. Virus is incubated with cells for 1 hour either at 37° C. or 33.5° C., the virus inoculum washed off in three washes with medium, and the cells re-fed and incubated at the respective temperature. Virus can be harvested in two approaches: either at 24 hours post-inoculation or at such time that cytopathic effects (rounding, detached and floating cells, destruction of the cell monolayer) are extreme. Virus titer is ascertained at the temperature at which the stocks were propagated. As the same number of cells and the same volume of medium is always employed, titers from successive passages can be directly compared in terms of infectious particles per mL or as a function of the number of cells.

Virus is used as a source of viral RNA. The viral RNA is reverse-transcribed, then the cDNA amplified with primers that flank the 234 site. The amplified fragment is directly sequenced, and the identity of the nucleotide at position 234 is determined. Similarly, the region surrounding the mutation in the polymerase is amplified, and the identity of the nucleotide at the mutated site(s) is determined.

As described in Example 1, we have demonstrated that mutations in the 5mer region nucleotide 232–236 (5CG-UUA) of CVB3/20 are stable when the mutated viruses are propagated at 33.5° C. but revert within 3–5 passages in cells at 37° C. At 37° C., there is a sudden 4–5 log increase in virus titer around pass 3–4 from a previously extremely low (less to much less than 500–750 TCID50/mL) titer. This sudden increase in titer correlates with the reversion of the mutated site(s) in the 5mer. No such sudden increase in titer is observed at 33.5° C. and no reversion from the mutated site is observed by sequence analysis out to pass 6. These differences in reversion at the different incubation temperatures can be used to define and compare respective reversion rates in pol-mutated and non-mutated virus.

Reversion rates of attenuated viruses can also be measured in vivo. Standard tests for reversion of attenuated viral vaccines involve measuring the reversion of the attenuating mutation in excreted virus particles. Such methods have been used to measure the reversion rate of attenuated poliovirus vaccines, wherein it was discovered that attenuated sites would mutate to produce reverted virus within 24 to 48 hours in fecal samples (Dunn et al., (1985) Nature 314(6011): 548–550; Macadam et al., (1989) Virology 172 (2): 408–414).

Measuring the reversion rate of pol mutants is first established in a suitable animal model, and thereafter can be used in humans. The mutant reporter strain is one selected to have a particularly high rate of mutation to quickly produce virus in feces that have a reverted genome. Pol mutations introduced into these test viruses can then be tested for any delay in reversion rate.

The extent of reversion in fecal samples is measured according to standard methods. Essentially, this involves plaquing virus from feces (to obtain clonal populations derived from one virus particle), then determining the sequence at attenuating sites for each plaqued stock. Results are quantified as reverted isolates per total clonal stocks plaqued.

The present invention is not limited to the embodiments described above, but is capable of modification within the scope of the appended claims.

We claim:

1. A coxsackievirus genome having a pol gene that encodes an RNA-dependent RNA polymerase, the genome being modified to produce an attenuated virus, the genome further comprising at least one pol gene modification that causes the polymerase to have increased fidelity as compared with a polymerase from a coxsackievirus genome that does not comprise the pol gene modification, wherein said pol gene modification results in an amino acid change in the RNA-dependent RNA polymerase selected from the group consisting of GLY328SER, GLY328CYS, GLY328ALA, GLY328LEU, GLY328ILE, TYR327PHE, LEU194VAL and GLU213GLY, wherein the increased fidelity results in a decreased reversion rate from attenuated virus to non-attenuated virus as compared with an equivalent coxsackievirus genome without the pol gene modification.

2. The coxsackievirus genome of claim 1, wherein the pol gene modification comprises a mutation resulting in an alteration of the RNA polymerase active site.

3. The coxsackievirus genome of claim 1, having a reversion rate at least two-fold decreased as compared with an equivalent virus without the pol gene modification.

4. A viral vector for delivering a heterologous nucleic acid to a target cell, tissue or organ, comprising the coxsackievirus genome of claim 1, said genome further comprising at least one cloning site for insertion of an expressible heterologous nucleic acid.

5. The vector of claim 4, comprising an expressible heterologous nucleic acid encoding an antigenic molecule.

6. The vector of claim 4, comprising an expressible heterologous nucleic acid encoding a biologically active molecule.

7. A live, attenuated viral vaccine comprising the coxsackievirus genome of claim 1.

8. The coxsackievirus genome of claim 1, which is a coxsackievirus B3 genome.

* * * * *